US00PP20047P3

(12) United States Plant Patent
Zary

(10) Patent No.: US PP20,047 P3
(45) Date of Patent: Jun. 2, 2009

(54) SHRUB ROSE PLANT NAMED 'JACMOUND'

(50) Latin Name: *Rosa hybrida*
Varietal Denomination: JACmound

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 133 days.

(21) Appl. No.: 11/824,566

(22) Filed: Jun. 28, 2007

(65) Prior Publication Data

US 2009/0031460 P1 Jan. 29, 2009

(51) Int. Cl.
*A01H 5/00* (2006.01)

(52) U.S. Cl. ..... Plt./107

(58) Field of Classification Search ..... Plt./107
See application file for complete search history.

*Primary Examiner*—Kent L Bell
(74) *Attorney, Agent, or Firm*—Klarquist Sparkman, LLP

(57) ABSTRACT

Shrub rose plant having flowers with excellent disease resistance; compact mounding plant habit; small, distinctive pink flowers with a white eye; excellent vigor on its own roots; constant bloom and cold hardiness to Zone 4.

1 Drawing Sheet

Genus and Species: *Rosa hybrida.*
Variety denomination: 'JACmound'.

ORIGIN OF THE INVENTION

The present invention relates to a new and distinct variety of a shrub rose plant named 'JACmound' which was originated by me by crossing an unnamed pink ground cover seedling, unnamed seedling×unnamed seedling, (unpatented) with the variety 'TANotax' (U.S. Plant Pat. No. 11,572).

BACKGROUND OF THE INVENTION

The primary objective of this breeding was to produce a new shrub rose variety having the compact rounded habit of the female (seed) parent with the excellent disease resistance of the male (pollen) parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Excellent disease resistance.
2. Compact mounding plant habit.
3. Small, distinctive pink flowers with a white eye.
4. Excellent vigor on its own roots.
5. Constant bloom.
6. Cold hardy to Zone 4.

Asexual reproduction of this new variety by cuttings, as performed at Wasco, Calif., shows that the foregoing characteristics and distinctions come true to form and are established and transmitted through succeeding propagations.

COMPARISON WITH PARENTS

The female seedling parent, differs in habit. The seedling female parent is a spreading ground cover rose. 'JACmound' is a compact, mounding shrub. 'TANotax' differs in flower color, pink for-the 'TANotax' parent versus pink with a white eye for the 'JACmound' variety.

COMPARISON WITH SIMILAR VARIETY

'JACmound' is believed to be most similar to 'RADcom' (U.S. Plant Pat. No. 15,070) except for flower color (solid pink for 'RADcom' versus pink with a white eye for 'JACmound').

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with the Royal Horticultural Society (London) Colour Chart© 2001, except where ordinary dictionary significance of color is indicated.

Parentage:

*Seed Parent.*—Unnamed pink ground cover seedling (not patented). Parentage is an unnamed seedling× unnamed seedling.

*Pollen parent.*—'TANotax' (U.S. Plant Pat. No. 11,572).

FLOWER

Observations made from January 2006 to June 2007 from plants commencing at two to three years of age grown in a garden environment at Somis, Calif.

Blooming Habit: Continuous.
Bud:

*Size.*—About 15 mm long and 8 mm in diameter when the petals start to unfurl.

*Form.*—The bud form is long, pointed ovoid.

*Color.*—When sepals first divide, bud color is Yellow-Orange Group 16D on the lower one-half of the bud and Red Group 46B on the upper one-half of the bud. When half blown, the upper sides of the petals are between Red Group 46B and 46C on the upper two-thirds and White Group 155D on the lower one-third and the lower sides of the petals are Red Group 55C on the upper two-thirds and Yellow Group 4D on the lower third.

*Sepals.*—Color: Upper surface: Green Group 138B. Lower surface: Yellow-Green Group 146A often with Greyed-Purple Group 183B. Length: 15 mm. Width: 6 mm. Shape: Subulate. Surface texture: Hoary. There are three lightly appendaged sepals. There are two unappendaged sepals with hairy edges.

*Receptacle.*—Color: Green Group 138B. Shape: Obovate. Size: Small, about 7 mm long×5 mm in diameter. Surface: Smooth.

*Peduncle.*—Length: Short, averaging about 25–30 mm. Surface: Glandular. Color: Green Group 138B sometimes overlaid with Greyed Purple Group 183B. Strength: Stiff, slender.

Bloom:

*Size.*—Small. Average open diameter is about 50 mm.

*Borne.*—In several together clusters of 3–7 blooms having pyramidal shape.

*Stems.*—Strength: Strong. Average length is about 100–150 mm with a diameter of 5–7 mm.

*Form.*—When first open: Flat. Permanence: Retains its form to the end.

*Petalage.*—Number of petals under normal conditions: 5–8. Color: The upper sides of the inner petals are between Red Group 46B and 46C on the upper two-thirds and White Group 155D on the lower one-third. The reverse sides of the inner petals are Red Group 55C on the upper two-thirds and Yellow Group 4D on the lower third. The base of the petals has a small 3 mm×3 mm Yellow Group 4B color spot. The major color on the upper sides is between Red Group 46B and 46C.

*Variegations.*—There are occasional streaks and splotches on petal surfaces.

*Discoloration.*—The general tonality at the end of the first day: No change. At the end of the third day: Color deepens to Red Group 46B and then drops. Further aging: No further change.

*Fragrance.*—Slight. Spicy.

Petals:

*Texture.*—Thick.

*Surface.*—Smooth.

*Shape.*—Obovate.

*Margin.*—Entire.

*Apex shape.*—Obcordate or obtuse.

*Base shape.*—Rounded.

*Form.*—Flat.

*Arrangement.*—Imbricated.

*Petaloid.*—Number: None, or occasionally 1–2. Color: Same as petal. Size: 1–3 mm wide; 3–7 mm long.

*Persistence.*—Petals drop off cleanly before drying.

*Lastingness.*—On the plant: Short (about 3 days). As a cut flower: Short (about 3 days).

Reproductive Parts:

*Stamens.*—Number: 50–60. Length: 4–6 mm. Anthers: Length: 1 mm. Color: Yellow-Orange Group 22A. Filaments: Color: Yellow Group 10C. Length: 3–5 mm. Pollen: Color: Greyed-Orange Group 164B.

*Pistils.*—Number: 30–35. Length: 3–4 mm. Styles: Color: Yellow-Green Group 146C. Length: 3 mm. Stigmas: Color: Yellow-Green Group 146D. Length: 1 mm.

*Hips.*—None observed.

PLANT

*Form.*—Shrub.

*Growth.*—Vigorous, branching, compact.

*Age to maturity.*—Two years.

*Mature plant.*—Height: 75 cm. Width: 75 cm.

*Rootstock.*—Own root.

Foliage: Number of leaflets on normal mid-stem leaves: 5 or more, often 7.

*Size.*—Small. About 110 mm long×70 mm wide.

*Quantity.*—Abundant.

*Color.*—New foliage: Upper side: Green Group 137C. Lower side: Green Group 137D. Old foliage: Upper side: Green Group 136A. Lower side: Green Group 137C.

Leaflets:

*Size.*—About 30 mm long×18 mm wide.

*Shape.*—Pointed oval.

*Base shape.*—Oblique.

*Apex shape.*—Acuminate.

*Texture.*—Leathery, glossy.

*Edge.*—Serrated.

*Serrations.*—Single.

*Petiole.*—Color: Green Group 136A.

*Petiole rachis.*—Color: Green Group 137C. Underside: Rough with prickles.

*Auricles.*—Subulate.

*Stipules.*—Length: 20 mm, serrated.

*Disease resistance.*—Resistant to mildew, rust and blackspot under normal growing conditions.

*Pest resistance.*—Not observed.

*Vein color.*—Green Group 137C.

*Venation pattern.*—Reticulate.

Wood:

*New wood.*—Color: Green Group 138C, often overlain with Greyed-Purple Group 183B. Bark: Smooth.

*Old wood.*—Color: Green Group 138C. Bark: Smooth.

Prickles:

*Quantity.*—On main canes from base: 20–25 per 150 mm of cane. On laterals from main canes: 20–25 per 150 mm of cane.

*Form.*—Hooked slightly downward.

*Length.*—7–10 mm.

*Color when young.*—Greyed-Purple Group 183B.

*Color when mature.*—Greyed-Red Group 174B.

Small Prickles:

*Quantity.*—On main stalks: None observed. On laterals: None observed.

Winter Hardiness: Hardy to Zone 4.

I claim:

1. A new and distinct variety of shrub rose plant, substantially as herein shown and described, characterized particularly by its compact mounding plant habit and small, distinctive pink flowers with a white eye.

* * * * *

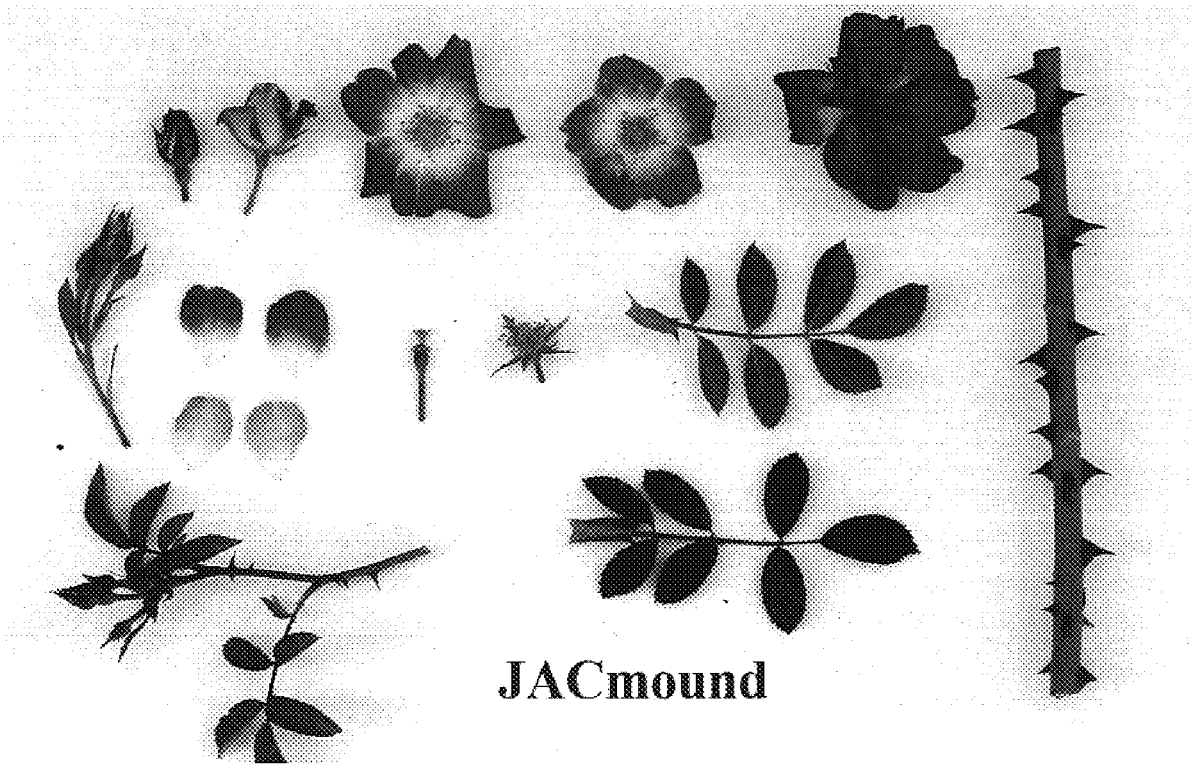
JACmound